United States Patent [19]

Straith

[11] 4,340,040
[45] Jul. 20, 1982

[54] NOSE SPLINT

[76] Inventor: Richard E. Straith, 625 Hillcrest Dr., Bloomfield Hills, Mich. 48013

[21] Appl. No.: 222,001

[22] Filed: Jan. 2, 1981

[51] Int. Cl.³ .............................................. A61F 5/08
[52] U.S. Cl. ................................ 128/76 C; 128/89 R
[58] Field of Search ............... 128/76 C, 89 R, 89 A, 128/87 R, 132

[56] References Cited

U.S. PATENT DOCUMENTS

| | | | |
|---|---|---|---|
| 1,378,455 | 5/1921 | Hilgers | 128/76 C |
| 2,509,157 | 5/1950 | Lind | 128/89 A |
| 3,426,751 | 2/1969 | Radewan | 128/76 C |
| 3,742,943 | 7/1973 | Malmin | 128/76 C |
| 4,213,452 | 7/1980 | Shippert | 128/89 R |

FOREIGN PATENT DOCUMENTS 18940 of 1908 United Kingdom .............. 128/76 C

Primary Examiner—John D. Yasko
Attorney, Agent, or Firm—Harness, Dickey & Pierce

[57] ABSTRACT

The disclosure relates to a nose splint usable to erect the lateral walls of the bony vault of the nose in a precise manner upon fracture thereof due to accident or rhinoplasty.

10 Claims, 5 Drawing Figures

NOSE SPLINT

BACKGROUND OF THE INVENTION

The human nose is essentially a pyramid that is divided into three compartments, namely, the bony vault, the upper cartilaginous vault, and the lower cartilaginous vault. The aforesaid vaults have a common supporting partition, the bony and cartilaginous septum.

The bony vault forms the principal structural base for the nose and is made up of upward projections of the frontal process of the maxilla from which a pair of nasal bones extend to form an arch at the union thereof. The posterior border of the bony vault is continuous with the maxilla. If the nose is thought of as being cantilevered, the bony vault forms a stable base, with its arch an extension of the skull. Stated in another manner, the bony vault with its cantilevered upper cartilaginous vault fuses with the dorsal edge of the septum to form a structural "I beam" extending from the radix of the skull to the lower cartilaginous vault.

The upper cartilaginous vault is made up of paired, triangular cartilages that extend from the bony vault as a cantilever and are attached along the dorsal border of the septum by a dense fibrous union. The cartilages are attached to the undersurface of the lateral walls of the bony vault by a membrane. The dorsal segment or upper edge of the upper cartilaginous vault is the bridge that connects the two upper lateral cartilages to give them stability.

The lower cartilaginous vault forms the base of the nose and is made up of tissues caudal to the free edge of the upper lateral cartilages. Although the lower vault is relatively independent of the vaults it shares with them the dorsal edge of the septum and the connective tissue attachments to the upper lateral cartilages.

Upon the occurrence of an accident the dorsum may be fractured or due to rhinoplasty the dorsum may be resected, separating the dorsal edge of the bony cartilaginous vaults from the walls thereof. At this point the cartilaginous vaults must rely on the remaining attachment to the nasal bones for their support. Thus, in order for proper healing to occur, the nasal pyramid must be fully and properly supported.

SUMMARY OF THE INVENTION

The invention relates to an improved splint for controlling fractured segments of the bony vault of the nose. The splint is constructed so as to maximize patient comfort and visual capability consistent with proper support of the nose. The splint is bendable to properly position and align pressure on the fractured or resected portion of the nose. Appurtenances on the splint provide for fastening of resilient elements that maintain proper pressure on the splint and provide for the support of auxiliary applicants.

DETAILED DESCRIPTION OF THE PREFERRED EMBODIMENT

Figure 1:
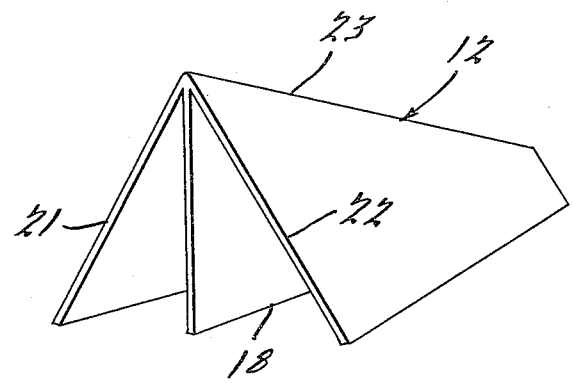
FIG. 1 is a diagrammatic representation of the nasal pyramid.
Figure 2:
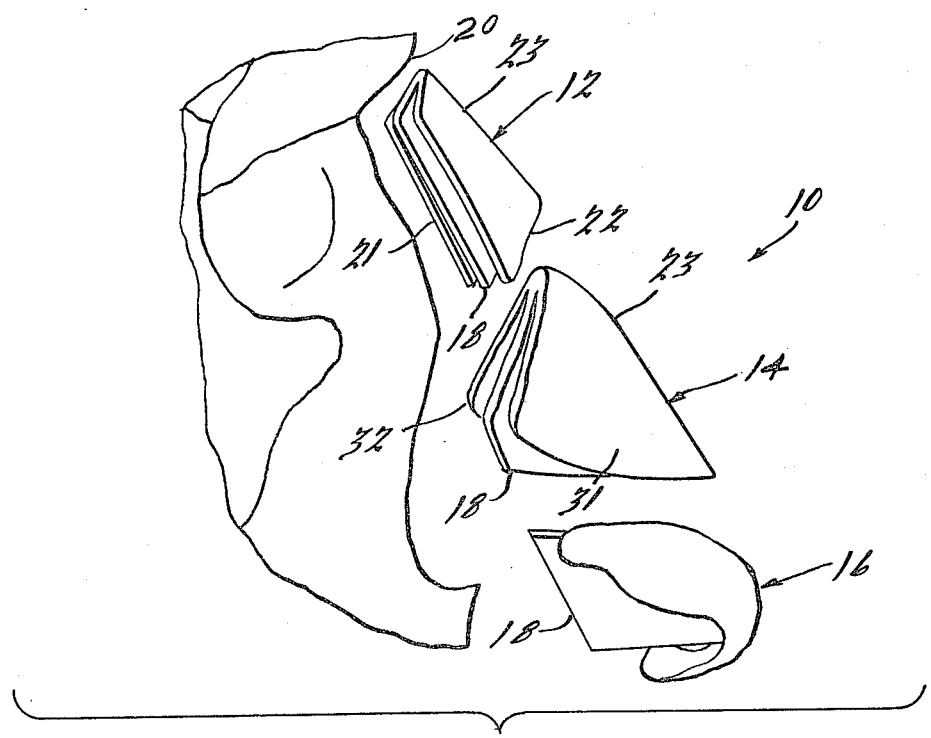
FIG. 2 is a perspective view of the three basic compartments of the nose.

As best seen in FIG. 2, the human nose 10 comprises the bony vault 12, the upper cartilaginous vault 14 and the lower cartilaginous vault 16. The vaults 12, 14 and 16 have a common supporting partition, the bony and cartilaginous septum 18.

The bony vault 12 is made up of upward projections of the frontal process of the maxilla 20, from which a pair of nasal bones 21 and 22 extend to form an arch at the union thereof. The upper cartilaginous vault 14 is made up of paired, triangular cartilages 31 and 32 that extend from the bony vault 12 and are attached along the dorsal border of the septum by a dense fibrous union. The cartilages 31 and 32 are attached to the undersurface of the lateral walls of the bony vault 12 by a membrane. The dorsal segment 23 or upper edge of the upper cartilaginous vault 14 is a bridge that connects the two upper lateral cartilages 31 and 32. The lower cartilaginous vault 16 forms the base of the nose 10 and is made up of tissues caudal to the free edge of the upper lateral cartilages 31 and 32. The lower vault 16 shares with the vaults 12 and 14 the dorsal edge 23 of the septum 18 and the connective tissue attachments to the upper lateral cartilages 31 and 32.

Upon the occurrence of an accident or incident to rhinoplasty, the septum 18 is separated from the dorsal edge 23 of the bony and cartilaginous vaults 12 and 14. Until healing occurs, the cartilaginous vaults 12 and 14 collectively define an open pyramid and must rely on the remaining attachment to the nasal bones 21 and 22 for their support and lateral distraction. In order to close the open pyramid or reconstruct a smaller pyramid, the nasal bones 21 and 22 must be positively supported at their bases. Therefore, the nasal bones 21 and 22 are fractured to reform the nasal pyramid 10.

Figure 3:
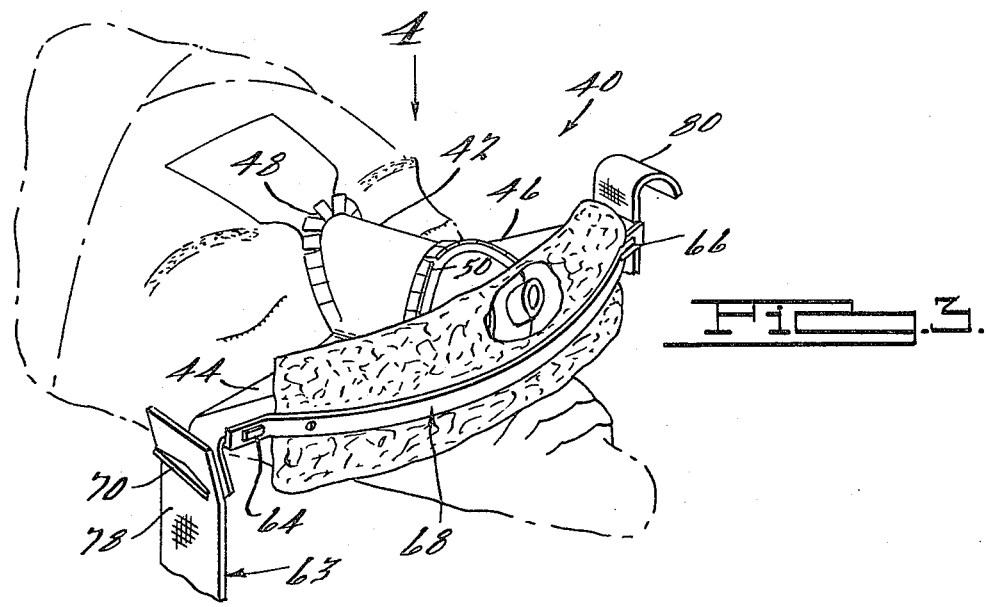
FIG. 3 is a perspective view of the splint of the instant invention in position so as to structurally support a patient's nose.
Figure 4:
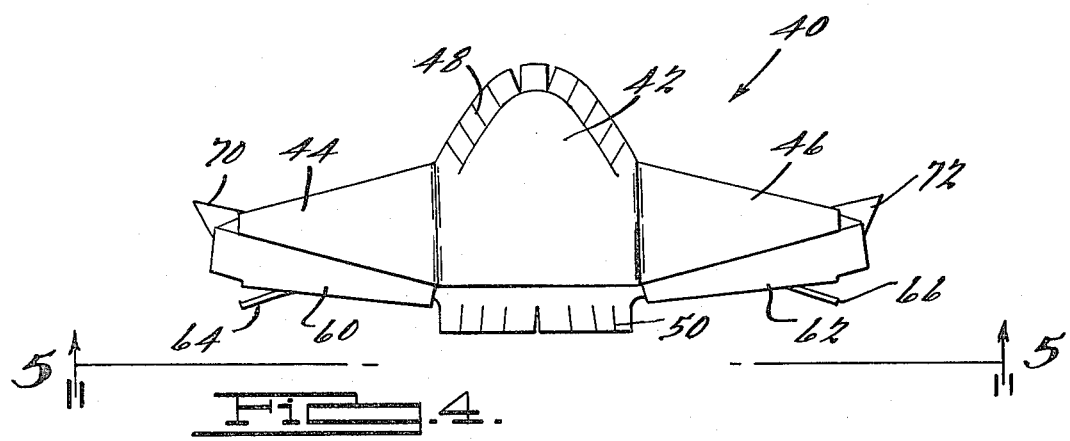
FIG. 4 is a view taken in the direction of the arrow 4 of FIG. 3.
Figure 5:
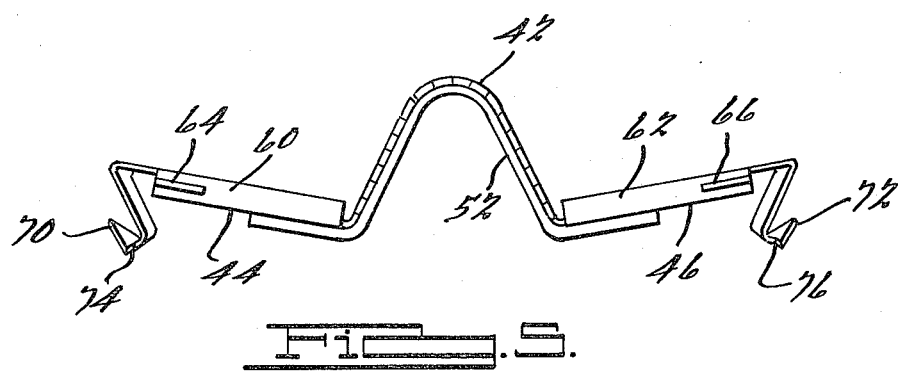
FIG. 5 is a view taken along the line 5—5 of FIG. 4.

As best seen in FIGS. 3, 4 and 5, a splint 40 in accordance with a constructed embodiment of the instant invention, is made from relatively ductile metallic sheet material, for example, aluminum which inherently also has some degree of flexibility and resiliency. The splint 40 is cut to the configuration best seen in FIG. 4 comprising an elongate bridge portion 42 of inverted U-shape in cross section and contoured to conform at least generally to the outer configuration of the human nose (FIG. 3) with elongated wing portions 44 and 46 extending laterally from the base thereof. The bridge portion 42 is of pyramid configuration in the sense that it comprises a broad-base structure that disposes the lower side edges of the bridge portion against the patient's cheeks at the base of the nose, as also shown in FIG. 3, and it is provided with a series of spaced slits 48 and 50 at the top and bottom thereof to faciliate forming the contour of the bridge to a particular patient's nose. It is to be noted that the wings 44 and 46 are tapered and displaced downwardly, as seen in FIG. 4, from the center of the bridge 42 to maximize a patient's visual capability and they incline slightly upwardly from the lower side edges of the bridge portion 42 as shown in FIG. 5 so that in the normal unstressed condition the wings clear or are spaced from the patient's cheeks.

As been seen in FIG. 5, the bridge portion 42 is arched, the underside of the arch being padded with a layer of foam rubber 52.

The wings 44 and 46 have reentrantly folded lower edge flanges 60 and 62 that function to stiffen the wings 44 and 46 and provide for positioning of the line of action of an external elastic 63, as will be described. The stiffening flanges 60 and 62 are folded about axes extending at substantially right angles to the axis of folding of the apex of the bridge portion 42 and they have fingers 64 and 66 extending therefrom, respectively, for the acceptance of a gauze supporting rubber sling 68. Pointed outer end portions or extensions 70 and 72 here shown on the stiffening flanges 60 and 62 of the wings 44 and 46 have barbs 74 and 76 thereon for penetration and retention of the end portions 78 and 80 of the elastic band 63 that extends from the points 70 and 72 under the patient's neck and the extensions 70 and 72 are bendable transversely of the wings to adjust and control the area of the patient's nose at which the elastic band 63 concentrates pressure imposed by the bridge 42 and to place a pre-determined downward pressure on the wings 44 and 46 which causes the lower edges of the bridge portion 42 to press against the patient's cheeks at the base of the nose.

In practice, tincture of benzoine is applied to the forehead and nasal bridge of the patient and allowed to dry. Surgical tape is then applied to the nasal skin after which the splint of the instant invention is superimposed over the patient's nose. The line of pressure of the splint on the nose is controlled by increasing or decreasing the angle of the reentrantly folded portions 60 and 62 of the wings 44 and 46 thereby to move the pointed end portions 70 and 72 upwardly or downwardly; viz., longitudinally with respect to the bridge portion 42, as seen in FIG. 4 of the drawing. It is to be noted that the relatively long lever arms provided by the wings 44 and 46 cause the lower edges of the bridge portion 42 to apply what may be termed a pinching action downwardly against the patient's cheeks and inwardly against the base of the nose through the padding layer 52, thereby to apply controlled pressure on the base of the nasal pyramid. Both the degree of pinching and total downward pressure of the splint is adjusted by first attaching one end of the elastic strap over either the point 70 or 72 of the splint 40. The elastic strap 63 is passed behind the patient's head and under the ears and stretched approximately 2.5 centimeters. Another slit is cut in the strap 63 at the point of engagement with the opposite wing, after which the strap 63 is engaged therewith. Stretching or extension of the elastic strap 63 in the manner described exerts a bias on the wings 44 and 46 to press the foam rubber lining 52 at the juncture of the bridge 42 and the wings 44 and 46 against the patient's cheeks adjacent to the nose and simultaneously to contract the bridge portion 42 so as to reduce the base dimension of the pyramid defined by the bridge portion and thereby exert a pinching action against the nose at the juncture thereof with the patient's cheeks as perhaps best shown in FIG. 3.

Gauze is held in place under the patient's nose by placing a pad sized approximately 1 inch by 4 inch under the nostrils and thereafter attaching the rubber sling 68 to the tabs 64 and 66 on the wings 44 and 46.

From the foregoing it should be apparent that the splint of the instant invention provides for a plurality of adjustments to assure proper positioning and retention of the bones of the nasal pyramid, as well as to provide for adjustment of the lines of force of the supplementary resilient members at the base and at opposite sides of the nose so as to prevent or at least inhibit bleeding into the operated area in the case of rhinoplasty. At the same time, the padding layer 52 at the juncture of the bridge portion 42 and the wings 44 and 46 provides a soft or yielding pressure that prevents pressure sores from developing at and along the lines of force. Adjustment is easily achieved by field bending of the splint 40 both to the particular contours of a patient's face and to accommodate the particular fracture or surgical process.

While it will be apparent that the preferred embodiment of the invention disclosed is well calculated to fulfill the objects above stated, it will appreciated that the invention is susceptible to modification, variation and change without departing from the proper scope of fair meaning of the subjoined claims.

What is claimed is:

1. A surgical splint for effecting controlled support of the nasal pyramid incident to fracture or dorsal resection thereof, said splint comprising a bridge portion of pyramid configuration, an elongated wing on each side of said bridge portion extending laterally from the base thereof, and means at the ends of said wings for attaching an elastic member for exerting a bias on said wings thereby to contract said bridge portion so to reduce the base dimension of said pyramid, the attaching means on said wings being disposed on a reentrantly folded portion to facilitate adjustment thereof.

2. A splint in accordance with claim 1 wherein the reentrantly folded portions on said wings are folded about axes extending at substantially right angles to the axis of folding of the apex of the bridge portion of said splint and whereby said attaching means are longitudinally adjustable to vary the location at which pressure is applied or concentrated against the nose.

3. A splint for a human nose that has been fractured because of an accident or as a result of rhinoplasty, said splint being of aluminum or other ductile material that also is flexible and resilient and having an elongate bridge portion of inverted U-shape in cross section contoured to conform at least generally to the outer configuration of the patient's nose so that when placed over the nose the lower side edges thereof are disposed alongside the base of the nose where the latter merges with the patient's cheeks;

wing portions extending laterally in opposite directions from respective lower side edges of said bridge portion and disposed to overlay and to angle normally upwardly away from the patient's cheeks;

an inner padding layer of foam rubber or the like on the sides of said bridge portion and extending around said lower side edges and along the undersides of said wing portions; and elastic means fastened to said wing portions adapted to extend therefrom around the back of the patient's head, the resilient action of said elastic means when stretched behind the head being operative to flex said wing portions downwardly and to press said padding layer with a yielding or resilient force against the cheeks at the base of the patient's nose and simultaneously to exert a pinching action against the nose to inhibit bleeding into the operated area.

4. A nose splint as defined by claim 3 including means for fastening said elastic means to said wing portions, said fastening means being bendable longitudinally of said bridge portion to vary the location at which pressure exerted by said elastic means is applied or concentrated against the patient's cheeks and nose.

5. A nose splint as defined by claim 3 including means for reinforcing and stiffening said wing portions.

6. A nose splint as defined by claim 5 wherein said reinforcing and stiffening means comprises the lower marginal edge portions of said wing portions bent out of the plane of said wing portions.

7. A nose splint as defined by claim 6 wherein said reinforcing and stiffening marginal edge portions overlay and are spaced from said wing portions.

8. A nose splint as defined by claim 7 wherein said fastening means are on and extend from said marginal edge portions.

9. A nose splint as defined by claim 4 or 8 wherein said fastening means comprise elongate extensions that are bendable transversely of the wings to adjust and control the point or area of the patient's nose at which said elastic means concentrates pressure by the bridge portion and at which the lower edges of the latter press on the patient's cheeks.

10. A nose splint as defined by claim 4 or 8 wherein said fastening means comprise elongate extensions that are bendable transversely of the wings to adjust and control the point or area of the patient's nose at which said elastic means concentrates pressure by the bridge portion and at which the lower edges of the latter press on the patient's cheeks; and cooperative interengaging means on said fastening means and said elastic means for detachably and adjustably interconnecting the same to vary the pull exerted by said elastic means on said fastening means.

* * * * *